United States Patent
Chung et al.

[11] Patent Number: 6,080,854
[45] Date of Patent: Jun. 27, 2000

[54] PROCESS FOR SYNTHESIZING CARBAPENEM INTERMEDIATES

[75] Inventors: John Y. Chung, Edison; Nobuyoshi Yasuda, Mountainside; Johnnie L. Leazer, Jr., Metuchen, all of N.J.

[73] Assignee: Merck & Co., Inc., Rahway, N.J.

[21] Appl. No.: 09/129,206

[22] Filed: Jul. 27, 1998

Related U.S. Application Data

[60] Provisional application No. 60/057,353, Aug. 25, 1997.
[51] Int. Cl.[7] .................................................. C07D 205/08
[52] U.S. Cl. ............................................................ 540/200
[58] Field of Search ............................................. 540/200

[56] References Cited

FOREIGN PATENT DOCUMENTS 0 451 764 A1  10/1991  European Pat. Off. .

OTHER PUBLICATIONS

Shiozaki, Tetrahedron 40(10) 1795, 1984.

S. M. Schmitt et al. J. Antibiotic, 41(6), p. 780–787 (1988).

*Primary Examiner*—Mark L. Berch
*Attorney, Agent, or Firm*—James M. Hunter, Jr.; Sylvia A. Ayler; Mark R. Daniel

[57] ABSTRACT

A process of synthesizing a compound of formula I is described:

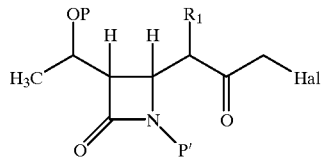

wherein P and P' independently represent H or a protecting group, $R_1$ represents H or $C_{1-4}$ alkyl, and Hal represents a halogen characterized by reacting a compound of formula 2:

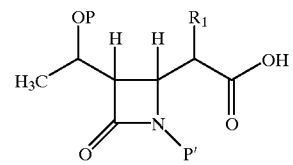

with $R_2OH$, wherein $R_2$ is $C_{1-4}$ alkyl, $C_{6-10}$ aryl or $C_{5-10}$ heteroaryl in the presence of an acid catalyst or carbodiimide reagent to produce a compound of formula 3:

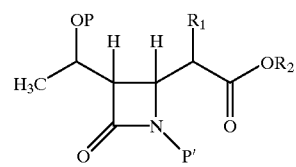

and reacting a compound of formula 3 in the presence of a base and a haloalkylating agent to produce a compound of formula 1.

12 Claims, No Drawings

PROCESS FOR SYNTHESIZING CARBAPENEM INTERMEDIATES

REFERENCE TO RELATED APPLICATION

This application claims the benefit of U.S. Provisional Application Ser. No. 60/057,353, filed Aug. 25, 1997.

BACKGROUND OF THE INVENTION

This invention relates to the synthesis of carbapenem intermediates. The invention is particularly useful in that it facilitates the presence of a β-methyl group upon cyclization to form the non-beta lactam ring of the carbapenem nucleus.

The side chain which is attached at position two of the carbapenem nucleus can be introduced prior to non-beta lactam ring cyclization. This reduces the number of steps which are necessary to produce the final compound. The side chain can be in protected or unprotected form, or a precursor of the side chain can be used, such as a coupling moiety, which can be present in protected or unprotected form prior to cyclization. This facilitates the addition of the side chain. Thus, the process described herein has extended utility, in that many different carbapenem antibiotics can be synthesized.

Prior syntheses of carbapenems have relied upon the very time consuming Mitsunobu reactions to synthesize the carbapenem framework. This invention responds to the need for a more convergent and facile procedure for synthesis of these compounds.

SUMMARY OF THE INVENTION

A process of synthesizing a compound of formula 1 is described:

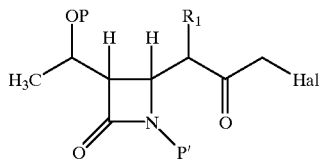

wherein P and P' independently represent H or a protecting group, $R_1$ represents H or $C_{1-4}$ alkyl, and Hal represents a halogen, comprising:
reacting a compound of formula 2:

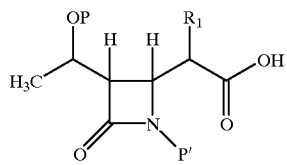

wherein P, P', and $R_1$ are defined above,
with $R_2OH$, wherein $R_2$ is $C_{1-4}$ alkyl, $C_{5-10}$ aryl or $C_{5-10}$ heteroaryl in the presence of an acid catalyst or carbodiimide reagent to produce a compound of formula 3:

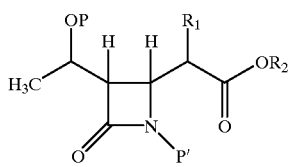

wherein P, P', and $R_1$ are defined above; and
reacting a compound of formula 3 in the presence of a base and a haloalkylating agent to produce a compound of formula 1.

This novel process allows for a more convergent and facile synthesis of antibiotics containing a carbapenem scaffold attached to nucleophilic sidechains through a methylene linkage.

DETAILED DESCRIPTION OF THE INVENTION

The invention is described herein in detail using the terms defined below unless otherwise specified.

The intermediate compounds synthesized in the present invention have asymmetric centers and occur as racemates, racemic mixtures, and as individual diastereomers. The processes of synthesizing all such isomers, including optical isomers, are included in the present invention.

In the invention described herein, a process of synthesizing a compound of formula 1 is described:

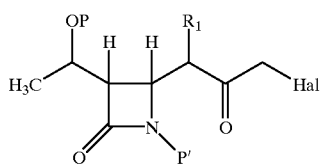

wherein P and P' each independently represent H or a protecting group; $R_1$ represents H or $C_{1-4}$ alkyl; and Hal represents a halogen selected from the group consisting of F, Cl, Br and I, comprising
reacting a compound of formula 2:

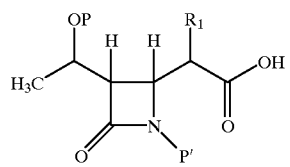

wherein P, P', and $R_1$ are defined above;
with $R_2OH$, wherein $R_2$ is $C_{1-4}$ alkyl, $C_{5-10}$ aryl or $C_{5-10}$ heteroaryl, in the presence of an acid catalyst or carbodiimide reagent to form a compound of formula 3:

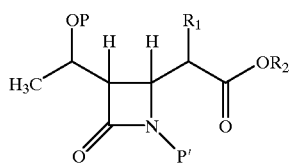

wherein P, P' and $R_1$ are as defined above, and reacting compound 3 in the presence of a base and a haloalkylating agent to produce a compound of formula 1.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al. *Protective Groups in Organic Synthesis* Wiley, New York (1991). Examples of suitable protecting groups are: t-butylmethylphenylsilyl, t-butyldiphenylsilyl, trimethylsilyl (TMS), triethylsilyl (TES), t-butyldimethylsilyl (TBS), o-nitrobenzyloxycarbonyl, p-nitrobenzyloxycarbonyl (PNZ), p-nitrobenzyl (PNB), benzyloxy-carbonyl, t-butyloxycarbonyl, 2,2,2-trichloroethyloxycarbonyl and allyloxycarbonyl. Preferred protecting groups are TBS, TMS and TES.

Examples of suitable aryl groups include aromatic rings e.g., phenyl, substituted phenyl and like groups as well as rings which are fused, e.g., naphthyl and the like. Aryl thus contains at least one ring having at least 5 atoms, with up to two such rings being present, containing up to 10 atoms therein, with alternating (resonating) double bonds between adjacent carbon atoms. The preferred aryl groups are phenyl and naphthyl.

Examples of suitable heteroaryl groups include monocyclic aromatic groups having 5 or 6 ring atoms, or bicyclic aromatic groups having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms. Examples are aromatic or partially aromatic groups such as thiophene, purine, imidazopyridine, pyridine, oxazole, thiazole, oxazine, pyrazole, tetrazole, imidazole, pyridine, pyrimidine and pyrazine and triazine.

Examples of suitable $R_1$ and $R_2$ alkyl groups include methyl, ethyl, n-propyl, isopropyl, n-butyl and t-butyl. Preferred $R_2$ alkyl groups are methyl, ethyl, propanol, isopropyl and t-butyl.

Examples of suitable acid catalysts include HCl, $H_2SO_4$, and 1-hydroxybenzotriazole hydrate (HOBT·$H_2O$), preferably 1-hydroxybenzotriazole hydrate (HOBT·$H_2O$).

Preferred carbodiimide reagents are 1,3-dicyclohexylcarbodiimide (DCC) and 1-(3-dimethylaminopropyl)-3-ethylcarbodiimide hydrochloride (EDC).

Examples of suitable bases can be selected from the group consisting of MeLi, s-BuLi and n-BuLi. Examples of suitable haloalkylating agents can be selected from the group consisting of $ICH_2Cl$, $BrCH_2Cl$, $TMSCH_2Cl$, and $TMSCH_2Br$. In a preferred aspect of this invention, the base is MeLi and the haloalkylating agent is $ICH_2Cl$. In another preferred aspect of this invention, the base is s-BuLi and the haloalkylating agent is $TMSCH_2Cl$.

Compound I is useful in the synthesis of carbapenem antibiotics. For example, compound I is useful in the synthesis of carbapenems such as those disclosed in EP Publication No. 0 451 764 A1 published on Oct. 16, 1991 as well as those carbapenems disclosed in Schmitt, et al., J. Antibiotics 41(6):780–787 (1988).

In a preferred embodiment of this invention a process for synthesizing a compound of formula 1 is described:

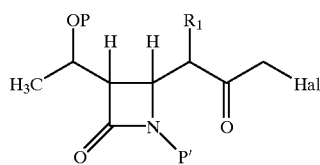

wherein:

P and P' independently represent trimethylsilyl, triethylsilyl or t-butyldimethylsilyl;

$R_1$ represents H or methyl;

and Hal represents Cl, Br or I;

comprising:

reacting a compound of formula 2:

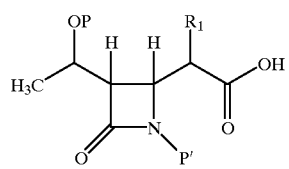

wherein P, P' and $R_1$ are defined above, with $R_2OH$, wherein $R_2OH$ is methanol, ethanol, propanol or isopropanol; in the presence of HOBT·$H_2O$, DCC, or EDC to produce a compound of formula 3:

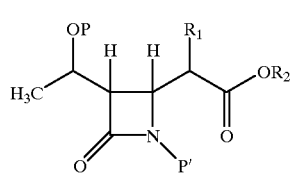

wherein P, P', and $R_1$ are defined above; and reacting a compound of formula 3 in the presence of MeLi and $ICH_2Cl$, or s-BuLi and $TMSCH_2Cl$, to produce a compound of formula 1.

The invention is illustrated in connection with the following non-limiting example.

EXAMPLE

Preparation of ethyl ester 2.

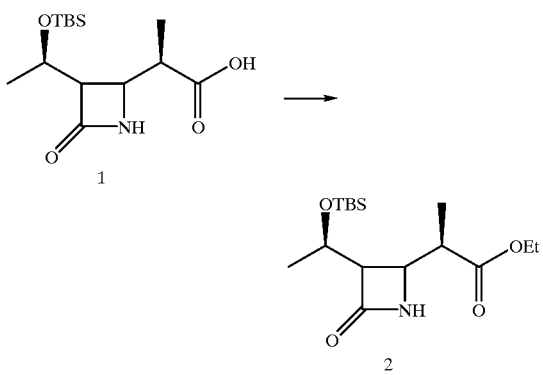

Carboxylic acid 1 (10.0 g, 33.2 mmol), HOBT-H$_2$O (6.7 g, 50.0 mmol), EtOH (85 mL), and EDC-HCl (9.6 g, 50.0 mmol) were allowed to age for 10 hours at ambient temperature. The resulting solution was poured into a mixture of 100 mL of CH$_2$Cl$_2$ and 40 mL of H$_2$O. The organic layer was washed with saturated aqueous Na$_2$CO$_3$ (50 mL), pH 7.0 phosphate buffer (100 mL), and brine (50 mL). The clear solution was dried over MgSO$_4$, and filtered through a small plug of MgSO$_4$. The material was then concentrated under reduced pressure to provide a crystalline solid (10.8 g) 98%: $^1$H NMR (250 MHz, CDCl$_3$) d 5.92 (1H, broad s), 4.19 (1H, m) 4.14 (2H, q, J=7.0 Hz), 3.88 (1H, dd, J=5.6 and 2.2 Hz), 2.97 (1H, ddd, J=4.2, 2.2, and 0.5 Hz), 2.68 (1H, qd, J=7.0 and 5.6 Hz), 1.26 (3H, t, J=7.0 Hz), 1.22 (3 H, d, J=7.2 Hz), 1.17 (3H, d, J=6.3 Hz), 0.86 (9H, s), and 0.06 (6H, s). $^{13}$C NMR (62.9 MHz, CDCl$_3$) d 174.1, 168.4, 65.1, 61.6, 60.8, 51.8, 42.7, 25.7, 22.4, 17.9, 14.1, 12.6, -4.4, and -5.1.

Preparation of chloromethyl ketone

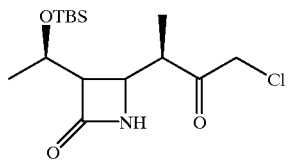

Method 1

Ethyl ester 2 (330 mg, 1.0 mmol), was dissolved in 5.0 mL of anhydrous THF and cooled to -78° C. Chloroiodomethane (529 mg, 3.0 mmol) and a 1.4M ether solution of MeLi (2.14 mL, 3.0 mmol) were added in portions over 2 hours. The resulting solution was then warmed to 0° C. and quenched with saturated aqueous NH$_4$Cl. The material was partitioned with EtOAc and washed with saturated aqueous Na$_2$S$_2$O$_3$ and brine. The clear solution was dried over MgSO$_4$, and filtered through a small plug of MgSO$_4$. The material was then concentrated under reduced pressure to a crystalline solid (230 mg) 69%: $^1$H NMR (250 MHz, CDCl$_3$): d 5.89 (broad s, 1H), 4.17 (m, 1H), 4.15 (s, 2H), 3.89 (dd, J=4.7 and 2.3 Hz, 1H), 3.20 (m, 1H), 2.92 (dd, J=4.9 and 2.3 Hz, 1H), 1.22 (d, J=7.3 Hz, 3H), 1.19 (d, J=6.7 Hz, 3H), 0.87 (s, 9H), 0.07 (s, 3H), and 0.06 (s, 3H). $^{13}$C NMR (62.9 MHz, CDCl$_3$) d 204.4, 168.3, 65.3, 61.7, 51.3, 47.6, 45.0, 25.7, 22.5, 17.9, 12.2, -4.3, -5.0.

Method 2

Chloromethyltrimethylsilane (368 mg, 3.0 mmol) was dissolved in 1.0 mL of anhydrous THF to form an anion solution. The solution was cooled to -78° C. s-BuLi (3.0 mmol, THF solution) was added dropwise while maintaining a reaction temperature of less than -70° C. A -78° C. solution of ethyl ester 2 (330 mg, 1.0 mmol) in 2.5 mL of anhydrous THF was added to the anion solution. The resulting mixture was allowed to age at -78° C. for 1 hour and then quenched at 0° C. with saturated aqueous NH$_4$Cl. The material was partitioned with EtOAc and then washed with water and brine. After drying over MgSO$_4$, the material was filtered and concentrated to a crystalline solid (80 mg) 24%.

What is claimed is:

1. A process of synthesizing a compound of formula 1:

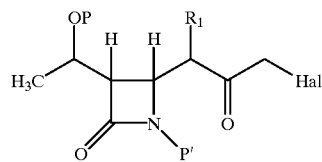

wherein P and P' independently represent H or a protecting group, R$_1$ represents H or C$_{1-4}$ alkyl, and Hal represents a halogen selected from the group consisting of F, Cl, Br and I, comprising:

reacting a compound of formula 2:

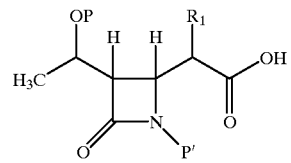

wherein P, P', and R$_1$ are defined above, with an alcohol of the formula, R$_2$OH, wherein R$_2$ is C$_{1-4}$ alkyl, C$_{6-10}$ aryl or C$_{5-10}$ heteroaryl in the presence of an acid catalyst or carbodimide reagent to produce a compound of formula 3:

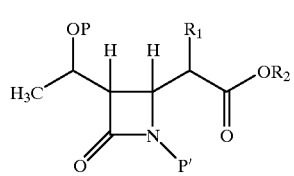

wherein P, P', and R$_1$ are defined above; and reacting a compound of formula 3 in the presence of a base and a haloalkylating agent selected from the group consisting of ICH$_2$Cl, BrCH$_2$Cl, TMSCH$_2$Cl, and TMSCH$_2$Br, wherein TMS is trimethylsilyl, to produce a compound of formula 1.

2. A process of synthesizing a compound of formula 1:

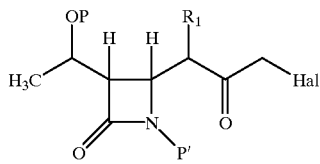

1 wherein:

P and P' independently represent trimethylsilyl, triethylsilyl or t-butyldimethylsilyl;

$R_1$ represents H or methyl;

and Hal represents Cl, Br or I;

comprising:

reacting a compound of formula 2:

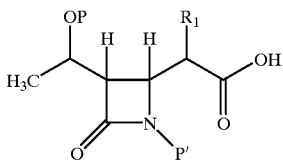

2 wherein P, P' and $R_1$ are defined above, with $R_2OH$, wherein $R_2OH$ is methanol, ethanol, propanol or isopropanol; in the presence of 1-hydroxybenzotriazole hydrate, DCC, or EDC to produce a compound of formula 3:

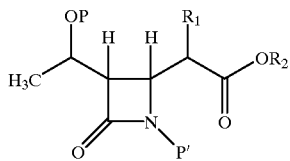

3 wherein P, P', and $R_1$ are defined above; and
reacting a compound of formula 3 in the presence of MeLi and $ICH_2Cl$, or s-BuLi and $TMSCH_2Cl$, to produce a compound of formula 1.

3. A process in accordance with claim 1 wherein $R_1$ is ethyl, ethyl, isopropyl or t-butyl.

4. A process in accordance with claim 1 wherein P and P' are independently selected from the group consisting of t-butylmethylphenylsilyl, t-butyldiphenylsilyl, trimethylsilyl, triethylsilyl, t-utyldimethylsilyl, o-nitrobenzyloxycarbonyl, p-nitrobenzyloxycarbonyl, p-nitrobenzyl, benzyloxy-carbonyl, t-butyloxycarbonyl, 2,2,2-trichloroethyloxycarbonyl and allyloxycarbonyl.

5. A process in accordance with claim 4 wherein P and P' are independently trimethylsilyl, triethylsilyl or t-butyldimethylsilyl.

6. A process in accordance with claim 1 wherein the alcohol is chosen from the group consisting of methanol, ethanol, propanol and isopropanol.

7. A process in accordance with claim 1 wherein the acid catalyst is selected from the group consisting of HCl, $H_2SO_4$ and 1-hydroxybenzotriazole hydrate.

8. A process in accordance with claim 7 wherein the acid catalyst is 1-hydroxybenzotriazole hydrate.

9. A process in accordance with claim 1 wherein the the carbodiimide reagent is DCC or EDC.

10. A process in accordance with claim 1 wherein the base is selected from the grolip consisting of MeLi, s-BuLi and n-BuLi.

11. A process in accordance with claim 10 wherein the base is MeLi and the haloalkylating agent is $ICH_2Cl$.

12. A process in accordance with claim 10 wherein the base is s-BuLi and the haloalkylating agent is $TMSCH_2Cl$.

* * * * *